United States Patent [19]

Agar

[11] Patent Number: 4,774,680
[45] Date of Patent: Sep. 27, 1988

[54] METHOD AND APPARATUS FOR NET OIL MEASUREMENT

[75] Inventor: Joram Agar, Grand Cayman, Cayman Islands

[73] Assignee: Agar Corporation, Ltd., Houston, Tex.

[21] Appl. No.: 909,626

[22] Filed: Sep. 19, 1986

[51] Int. Cl.[4] .................. G01N 15/00; G01N 27/00; G01F 1/74

[52] U.S. Cl. .................. 364/550; 73/61 R; 73/861.04; 324/71.1; 324/61 P; 324/65 R

[58] Field of Search .............. 364/550, 551, 496, 497, 364/498, 508; 324/61 R, 61 P, 65 R, 65 P, 71.1, 76 R, 439, 445; 328/1; 73/61 R, 153, 861.04

[56] References Cited

U.S. PATENT DOCUMENTS

| | | | |
|---|---|---|---|
| 3,006,189 | 10/1961 | Warren et al. | 73/861.04 |
| 3,025,464 | 3/1962 | Bond | 324/61 P |
| 3,200,312 | 8/1965 | Callahan | 361/280 |
| 3,368,147 | 2/1968 | Graham | 324/61 P |
| 3,385,108 | 5/1968 | Rosso | 73/861.04 |
| 3,523,245 | 8/1970 | Love et al. | 324/61 R |
| 3,550,019 | 12/1970 | Thomas | 307/308 |
| 3,559,830 | 3/1971 | Gass | 324/78 |
| 4,112,744 | 9/1978 | Tassano | 324/61 R X |
| 4,240,028 | 12/1980 | Davis, Jr. | 324/61 R |
| 4,266,188 | 5/1981 | Thompson | 324/61 R X |
| 4,429,273 | 1/1984 | Mazzagatti | 324/61 R |
| 4,434,233 | 2/1984 | Bzdula | 324/439 X |
| 4,559,493 | 12/1985 | Goldberg et al. | 73/61.1 R X |
| 4,644,263 | 2/1987 | Johnson | 324/65 P |
| 4,701,713 | 10/1987 | Eaton et al. | 324/439 X |
| 4,713,603 | 12/1987 | Thorn | 324/61 P |

Primary Examiner—Parshotam S. Lall
Assistant Examiner—Joseph L. Dixon
Attorney, Agent, or Firm—Pravel, Gambrell, Hewitt, Kimball & Krieger

[57] ABSTRACT

Disclosed is a method and apparatus for measuring the percentages of oil and water present in an oil/water mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixture yields a current output which can be plotted on one of two distinct, empirically or theoretically derived, data curves. One of the data curves represents oil being in the continuous phase and the other data curve represents water being in the continuous phase. A comparator is used to determine whether the oil or the water is in the continuous phase to thereby select the proper data curve on which the energy absorption is plotted. Each of the curves has the energy absorption properties of the media plotted against the percentage of water. Plotting the amount of energy absorbed on the proper curve yields the percentage of water present.

16 Claims, 2 Drawing Sheets

METHOD AND APPARATUS FOR NET OIL MEASUREMENT

FIELD OF THE INVENTION

The present invention relates to a method for determining the amount of oil in an oil/water mixture.

BACKGROUND OF THE INVENTION

The accuracy of net oil measurement is extremely important to buyers and sellers of oil. If the oil contains water, the buyer does not want to pay for the gross amount of liquid shipped to him. Rather, he is to pay only for the net amount of oil present in the total volume delivered. Net oil measurement is also required in oil fields for royalty payments and in enhanced oil recovery fields for pumping rate control.

There are in the prior art a number of instruments which have been used to measure water content in an oil/water mixture. Most of such instruments in the prior art rely on the difference between the dielectric constant of water and the dielectric constant of oil. As such, the main problem with these devices is their inability to deal with mixtures where the water constituent of the mixture is in the continuous phase rather than the oil. By definition, the dielectric constant is the ratio of the capacitance of a capacitor field with a given dielectric to that of the same capacitor having only a vacuum as the dielectric. Therefore, in using the devices for oil/water measurement, when water is the continuous phase the instrument will peg at full scale because the electric path between the two parallel plates of the capacitor will be shorted by the water in continuous phase. This is so even though oil may still comprise some 40 to 50 percent or more of the overall mixture.

A relatively typical capacitance probe for use in determining oil/water ratios is found in U.S. Pat. No. 3,200,312 to Callahan. Callahan relies on the measurement of the mixture's dielectric constant. As such, the probe must be non-functional when water is in the continuous phase.

Yet another capacitance-type probe is taught in U.S. Pat. No. 3,025,464 to Bond. The Bond probe is designed specifically for pipeline use where there is typically low water content and oil is in the continuous phase. For that purpose, the Bond probe will function adequately. However, because the Bond probe is a capacitance probe, it will not function in mixtures where water becomes the continuous phase.

Still another prior art capacitance probe is shown in U.S. Pat. No. 3,523,245 to Love et al. It has the same shortcomings as the prior art references mentioned above. In fact, FIG. 2 of the Love et al patent depicts a graph for water fraction versus probe capacitance. It is noted that the water fraction portion of the graph does not go above 0.5. In fact, the Love et al reference in discussing FIG. 2 specifically states that when the water fractions get above 0.5, the water tends to separate out and the capacitance quickly approaches the value at free water.

U.S. Pat. No. 3,368,147 to Graham teaches a capacitance measuring circuit to determine the sediment and water content of oil well production. Because Graham relies on capacitance, such reference is also insufficient to determine oil/water ratios where water is in the continuous phase.

U.S. Pat. No. 3,550,019 to Thomas seems to teach a linearizing circuit for net oil analyzers. However, Thomas does not teach the use of a digital linearizer or any means of overcoming the jump in the electrical characteristic of the mixture as the oil/water mixture moves from oil being in the continuous phase to water being in the continuous phase.

Yet another net oil computer is described in U.S. Pat. No. 3,385,108 to Rosso. Rosso relies on a capacitance probe and does not teach the use of a digital linearizer or any means of overcoming the jump in the electrical characteristic of the mixture when the oil/water mixture goes from oil being in the continuous phase to water being in the continuous phase.

Another typical capacitance probe having the same inadequacies as those probes mentioned above is found in U.S. Pat. No. 3,006,189 to Warren et al.

SUMMARY OF THE INVENTION

It is therefore an object of the present invention to provide an apparatus and method for determining the percentage of water present in a mixture where either oil or water is in the continuous phase.

Yet another object of the present invention is to provide an apparatus and method for determining the percentage of water in an oil/water mixture where the amount of water present is in the range from 0 to 100 percent.

Still a further object of the present invention is to provide a method and apparatus for determining the water content in oil/water mixtures by measurement of the mixtures' electrical properties wherein the output signal is linearized.

Still another object of the present invention is to teach a method and apparatus for determining whether oil or water is in the continuous phase by measuring an electrical property of the mixture.

Yet a further object of the present invention is to provide a method and apparatus for selecting one of two curves which represent the possible conditions of the media.

It is a further object of the present invention to provide an apparatus and method for determining the percentages of oil and water in an oil/water mixture by measuring its electrical properties wherein it is determined whether the oil or the water is in the continuous phase.

Yet another object of the present invention is to provide two empirically or theoretically derived curves which plot percentage of water versus current which allows determination of whether the oil or the water is in the continuous phase.

Briefly stated, the foregoing and numerous other features, objects and advantages of the present invention will become readily apparent upon reading the detailed description, claims and drawings set forth hereinafter. These features, objects and advantages are accomplished by utilizing a microprocessor or comparator circuit which is able to distinguish between oil being in the continuous phase and water being in the continuous phase based on the electrical properties of the mixture. A few techniques are available to measure the electrical properties of the mixture. For example, the conductivity of the media may be measured at a high frequency. While these techniques avoid the saturation effect which is typical of measuring capacitance, they produce two distinct, non-linear curves of output signal typically plotting current versus the percentage of water in the mixture. These curves may be empirically or theoretically derived. The first of these curves is for the case where the water is in the continuous phase, while the second curve occurs where oil is the continuous phase. It should be understood that the change in phase does not occur at a predetermined oil/water ratio. Other variables are involved, including droplet size, surface tension and emulsifying chemicals present. Typically however, the change occurs when the amount of water present in the mixture is in the range of 35 to 75 percent of the total. Thus, just measuring the energy absorption properties of the mixture is not the complete solution. Because there are two distinct curves or equations it is necessary to determine which curve or equation is to be used in calculating the percentage of water present.

As noted earlier, the step jump occurs in the data when the mixture changes over from oil being in the continuous phase to water being in the continuous phase. It is very desirable to eliminate this step jump from the data and to linearize the two distinct curves.

It should be apparent that the step change represents a rapid jump in the mixture's conductivity. This change in conductivity is measured by a conductivity meter or energy absorption detector usually in units of milliamps of output. This information is fed to a comparator to select one of two memories, those being where water is in the continuous phase and where oil is in the continuous phase. Generally, it has been determined that if the oil/water monitor in a particular configuraiton measures a current of say, less than 5 milliamps, then oil is in the continuous phase and if a current greater than 5 milliamps is measured then water is in the continuous phase. The linearized output from the selected memory is fed to an output stage, display or multiplier. The multiplier is used to determine the net water by multiplying the gross flow rate by the percentage of water present. The difference between the gross flow rate and the net water equals the net oil present.

DESCRIPTION OF THE PREFERRED EMBODIMENT

Figure 1:
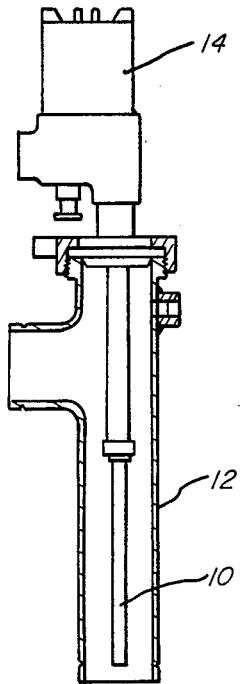
FIG. 1 is an elevational view of a probe and oil/water monitor as used in conjunction with the present invention.

Turning first to FIG. 1 and there is shown a probe 10 mounted within a conduit 12. Energy is transmitted into the medium from oil/water monitor 14 through probe 10. In such manner, oil/water monitor 14 can measure the electrical properties of the media flowing through conduit 12. Typically, this could be performed by measuring the conductivity, energy absorption, capacitance, admittance and/or impedance of the media with oil/water monitor 14. As used herein the term "electrical properties" includes all of such terms singly or in combination.

One such oil/water monitor 14, which can be used with the present invention, is the Agar OW-101 water in oil monitor.

The Agar OW-101 measures the energy absorption properties of the oil/water mixture, rather than just the capacitance. It is used in conjunction with an empirically generated curve plotting milliamps versus percentage of water. The curve contains a pronounced step jump as the mixture goes from oil being in the continuous phase to water being in the continuous phase. Because the location of the step is affected by a number of variables, it can be difficult to determine precisely what pecentage of water is present.

Another device which may be used for oil/water monitor 14 is the Invalco Model No. CX-745-200GP.

U.S. Pat. No. 4,503,383 to Agar et al teaches another device which can be used in the capacity of oil/water monitor 14.

Figure 4:
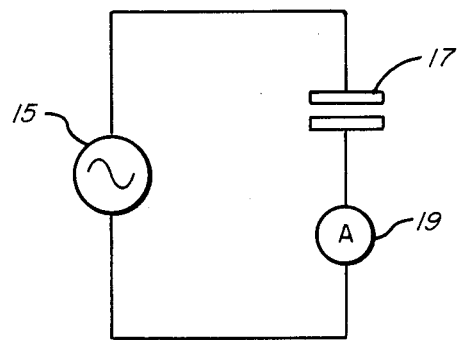
FIG. 4 is a schematic of a circuit for an oil/water monitor.

Still another device which can be used as oil/water monitor 14 is shown schematically in FIG. 4. It includes an alternating current generator 15, a capacitor 17 and an ammeter 19. The capacitor 17 should be in the form of a probe inserted into the fluid. The ammeter 19 measures current [I]so that when water is in the continuous phase the circuit can be defined by the equation:

$$I = V/R$$

which is Ohm's Law, where I is the current through the ammeter 19, V is the voltage of the generator 15, and R is the effective resistance of the media.

When oil is in the continuous phase the circuit can be defined by the equation:

$$I = Vjwc$$

where "j" is the square root of $-1$, "w" represents the radial frequency and "c" represents capacitance of the probe with the mixture inside it. Thus there can be theoretically derived two distinct curves or equations representing some electrical property plotted against the percentage of water present. It is known that the effective capacitance of a parallel plates capacitor is given by the equation:

$$C = KEA/D$$

where "C" is effective capacitance, "K" is a dimensional constant, "E" is the dielectric constant of the media between the plates, "A" is the area of the plates and "D" is the distance between the plates. It is further known that the effective resistance of a media contained between two plates is given by the equation:

$$R = D/AG$$

where "R" is the effective resistance, "D" is the distance between the plates, "A" is the area of the plates and "G" is the conductivity of the media. Because both the dielectric constant and the conductivity of the media are proportional to the percentage of water present in media, the derivation of two distinct equations is possible. However, the dielectric constant and conductivity of the media depend not only on the percentages of water and oil present, but also on which constituent is in the continuous phase. As mentioned earlier, the constituent which is in the continuous phase is affected by a number of other variables. Therefore, it is probably simpler to use the empirically generated curves shown in FIG. 3.

The current or electrical signal generated in oil/water monitor 14 is transmitted to a zero to span adjuster 16 which allows the device of the present invention to be calibrated. From the zero to span adjuster 16 the data is transmitted to an analog to digital converter 18 and to a comparator 20. The comparator 20 uses this information to select one of two memories. There is a continuous water phase memory 22 and a continuous oil phase memory 24.

Figure 3:
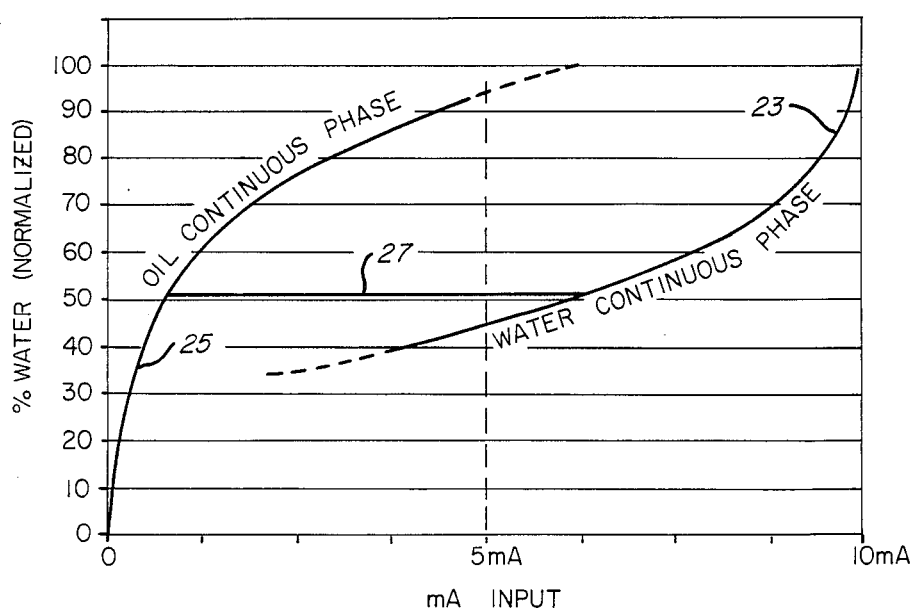
FIG. 3 is a graph of the two empirically derived curves plotting current absorbed or admittance versus percentage of water.
Figure 2:
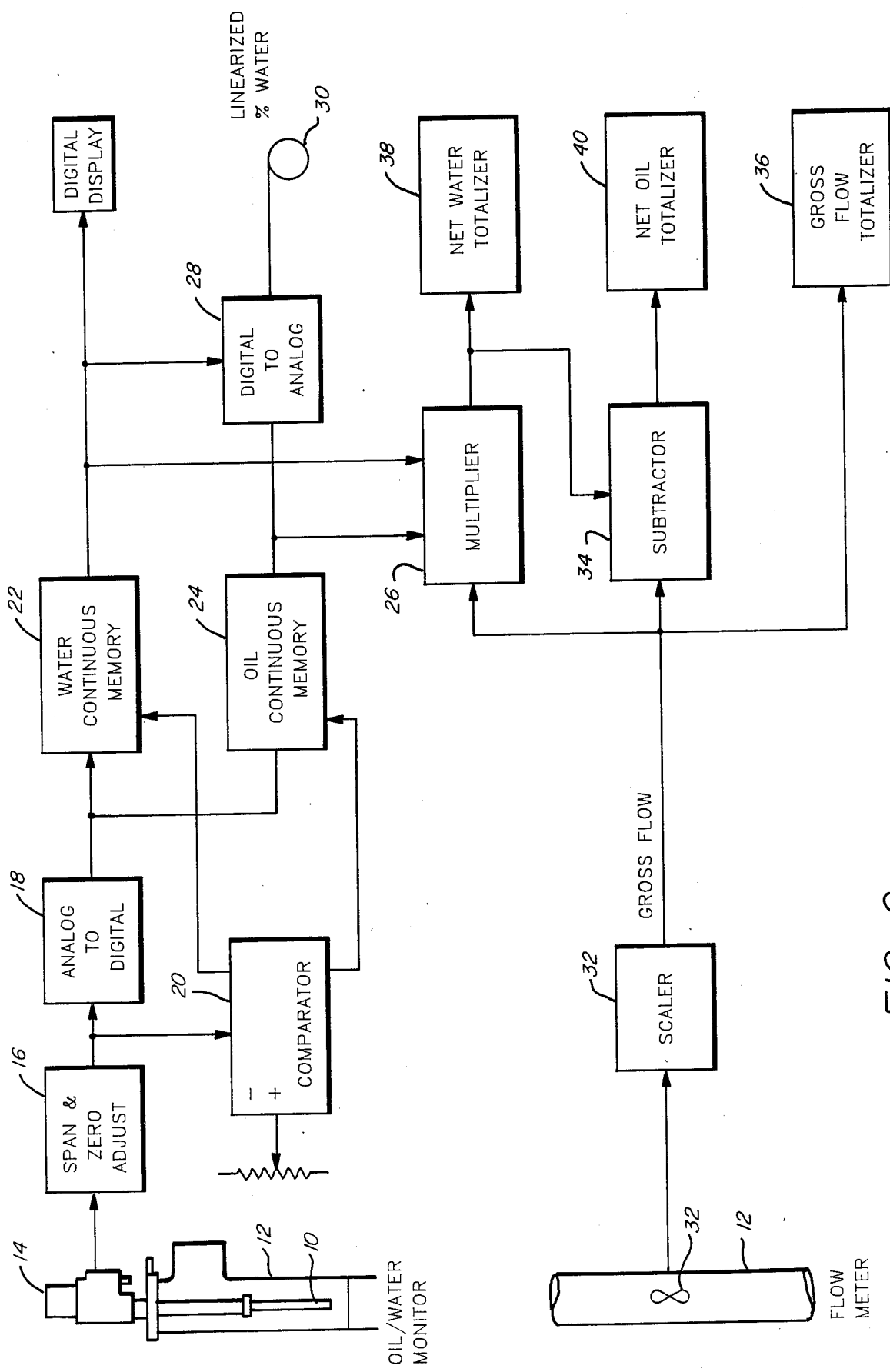
FIG. 2 is a schematic diagram of the flow of data through the apparatus of the present invention.

The continuous water phase memory 22 and the continuous oil phase memory 24 represent curves 23 and 25 respectively as shown in FIG. 3. These curves can be arrived at empirically, or theoretically. Curves 23 and 25 plot some electrical signal versus percentage of water present in the mixture. The electrical signal may be in the form of a measurement of current, voltage, frequency, energy, conductivity, capacitance, admittance, impedance or the like. It should be recognized that curves 23 and 25 represent two separate and distinct equations. Note that curves 23 and 25 have been projected past the points where they intersect the step jump 27 as shown by the dashed lines. The comparator 20 is, in actuality, a microprocessor or other computing device which compares the measured electrical signal shown in FIG. 3 as current with a preset value, say 5 milliamps. If the measured current is greater than the preset value, then water is in the continuous phase and the comparator 20 selects water continuous phase memory 22 with data plotted as the upper milliamperage curve 23. If the measured current is less than the preset value, then the oil is in the continuous phase and the comparator 20 selects oil continuous phase memory 24 containing data plotted as the lower milliamperage curve 25.

The data transmitted from the oil/water monitor 14 provides the comparator 20 with the amount of current measured so that the comparator 20 can compare that value to the preset value.

Depending on which continuous memory 22 or 24 is selected, the data is transmitted from analog to digital converter 18 to that particular phase memory 22 or 24 where the amount of current is used to determine the percentage of water present by way of curve 23 or curve 25. The digitized data representing the percentage of water present is then transmitted to multiplier 26 and simultaneously, to a digital to analog converter 28. The data from the digital to analog converter 28 is then transmitted to a meter 30 where the percent of water can be directly read.

The flow rate of the oil/water mixture flowing through conduit 12 is measured by flow meter 32. Flow meter 32 is preferably a positive displacement type flow meter or of some other type of high accuracy type flow meter. Output from flow meter 32 is transmitted simultaneously to multiplier 26, subtractor 34 and gross flow totalizer 36. Gross flow totalizer 36 keeps a running tabulation of the total volume pumped through conduit 12. The gross flow data transmitted from flow meter 32 to multiplier 26 is multiplied by the percentage of water data transmitted to multiplier 26 from memories 22 and 24. The data is then transmitted from multiplier 26 simultaneously to net water totalizer 38 and to subtractor 34. Net water totalizer 38 keeps a running tabulation of the total amount of water which has been pumped through conduit 12. Within subtractor 34, the total water volume is subtracted from the gross flow with the result being transmitted to the net oil totalizer 40. Net oil totalizer 40 keeps a running tabulation of the total volume of oil which has been pumped through conduit 12.

FIG. 3 is a graph depicting a somewhat typical step jump 27 between the two non-linear curves 23 and 25 generated when oil/water ratios are determined by measuring the electrical properties of the mixture. It is highly desirable to eliminate the step jump from the data. It is also highly desirable to linearize the data. The present invention accomplishes these goals through the use of comparator 20, and memories 22 and 24, and analog to digital converter 18. Further, by relying on other electrical properties ties of the media such as energy absorption, rather than the dielectric constant alone, the present invention allows measurement of the ratio of oil to water regardless of which component is in the continuous phase up to and including the situation where there is no true mixture and 100 percent of the volume is water.

For purposes of clarification, the component in the continuous phase can be defined as that liquid which contains and surrounds the droplets of the second liquid such that the second liquid is present within the first liquid in the form of individual, discreet units.

It should be understood that, the comparator circuit of the present invention is useful in evaluating data in any two curve situation where automatic identification of the proper curve is necessary. An example would be a conventional turbine flow meter. The comparator circuit, taught herein, could be used to distinguish between laminar and turbulent flow, and correct the "meter factor" accordingly.

From the foregoing, it will be seen that this invention is one well adapted to obtain all of the ends and objects hereinabove set forth, together with other advantages which are apparent and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

What is claimed is:

1. A comparator circuit for use in determining phase conditions of fluids where there is a pronounced step jump joining two independent curves, such as in the electrical properties of an oil/water mixture or the flow characteristics of a fluid, said comparator circuit receiving data from a probe device such as an oil/water monitor or a turbine flow meter, comprising:
   a. a first memory for storing a first data curve representing a first set of phase characteristics;
   b. a second memory for storing a second data curve representing a second set of phase characteristics; and
   c. a computer means for receiving the data from the probe device, said computer means comparing the data received to a predetermined value, thereby allowing said computer means to select said first memory if the data received from the probe device is less than the predetermined value or to select said second memory if the data received from the probe device is greater than the predetermined value.

2. A method for measuring the percentage of water present in an oil/water mixture, comprising the steps of:
   a. measuring an electrical property of the oil/water mixture with an oil/water monitor;
   b. determining whether the oil of the water is in the continuous phase in the mixture;
   c. selecting one of two data curves, each of said data curves having an electrical signal plotted against the percentage of water, one of said data curves representing water being in the continuous phase and the other of said data curves representing oil being in the continuous phase; and
   d. reading the selected data curve to determine the percentage of water pesent in the mixture.

3. A method for measuring the percentage of water present in an oil/water mixture flowing through a conduit, comprising the steps of:
   a. measuring an electrical property of the oil/water mixture with an oil/water monitor;
   b. determining whether the oil or the water is in the continuous phase in the mixture;
   c. selecting one of two data curves, each of said data curves having an electrical signal plotted against the percentage of water, one of said data curves representing water being in the continuous phase and the other of said data curves representing oil being in the continuous phase; and
   d. reading the selected data curve to determine the percentage of water present in the mixture.

4. A method for measuring the percentage of water present in an oil/water mixture flowing through a conduit as recited in claim 3, further comprising the steps of:
   a. measuring the gross flow of the oil/water mixture through the conduit; and
   b. multiplying the gross flow by the percentage of water to totalize the volume of water flowing through the conduit.

5. A method for measuring the percentage of water present in an oil/water mixture flowing through a conduit as recited in claim 4, further comprising the step of:
   subtracting the totalized volume of water from the gross flow to determine the total volume of oil flowing through the conduit.

6. A method for measuring the percentage of water present in an oil/water mixture utilizing two distinct data curves which represent water being in the continuous phase and oil being in the continuous phase, respectively, comprising the steps of:
   a. measuring an electrical property of the oil/water mixture and generating an electrical signal;
   b. comparing the measured value of the electrical property to a predetermined value for determining whether the oil or the water is in the continuous phase in the mixture, thereby selecting one of the two distinct data curves, each of the two distinct data curves having the electrical signal plotted against percentage of water;
   c. digitizing the electrical signal of the measurement of the electrical property as determined in said measuring step; and
   d. plotting the digitized electrical signal on the curve selected to thereby determine the percentage of water present in the mixture.

7. An apparatus for measuring the percentage of water present in an oil/water mixture, comprising:
   a. a probe disposed in the oil/water mixture;
   b. means for measuring the electrical properties of the oil/water mixture, said means for measuring being electrically connected to said probe;
   c. a first memory for storing a data curve representing water being in the continuous phase in the mixture;
   d. a second memory for story a data curve representing oil being in the continuous phase in the mixture; and
   e. a comparator means for determining whether the oil or the water is in the continuous phase in the mixture by comparing the amount of energy absorbed to a predetermined value, thereby allowing said comparator means to select said first or said second memory and its respective data curve, each of said data curves having energy absorption plotted against the percentage of water in the mixture.

8. An apparatus for measuring the percentage of water present in an oil/water mixture flowing in a conduit, comprising:
   a. a probe disposed in the oil/water mixture;
   b. means for measuring the electrical properties of the oil/water mixture, said means for measuring being electrically connected to said probe;
   c. a first memory for storing a data curve representing water being in the continuous phase in the mixture;
   d. a second memory for storing a data curve representing oil being in the continuous phase in the mixture; and
   e. a comparator means for determining whether the oil or the water is in the continuous phase in the mixture by comparing the amount of measured electrical signal to a predetermined value, thereby allowing said comparator means to select said first or said second memory and its respective data curve.

9. An apparatus for measuring the percentage of water in an oil/water mixture flowing through a conduit as recited in claim 8, further comprising:
   a. a flow meter for measuring the gross flow through the conduit; and
   b. a multiplier means receiving data from said first and said second memories and said flow meter to thereby obtain the product of the gross flow and the percentage of water.

10. An apparatus for measuring the percentage of water present in an oil/water mixture flowing through a conduit as recited in claim 9, further comprising:
    a subtraction means for subtracting the data generated by said multiplier means from the gross flow.

11. An apparatus for measuring the percentage of water present in an oil/water mixture flowing through a conduit as recited in claim 10, further comprising:
    a gross flow totalizer.

12. An apparatus for measuring the percentage of water present in an oil/water mixture as recited in claim 8, further comprising:
    an analog to digital converter for digitizing the data generated by said means for measuring before it is transmitted to said first and said second memories.

13. An apparatus for measuring the percentage of water present in an oil/water mixture as recited in claim 12, further comprising:
    a digital to analog converter for translating the digitized data from said memories to continuous analog signals.

14. A method for linearizing data generated by an oil/water monitor and computing the percentage of water present in an oil/water mixture, comprising the steps of:
- a. transmitting a current into the mixture;
- b. measuring an electrical property of the mixture with an oil/water monitor;
- c. comparing the measured electrical property to a predetermined value to thereby select one of two data curves, each curve having an electrical signal plotted against percentages of water, one data curve representing oil in the continuous phase in the mixture and the other data curve representing water in the continuous phase in the mixture; and
- d. plotting the measured electrical property on the selected curve.

15. In combination with an oil/water monitor which generates data of the electrical properties of an oil/water mixture, a method for determining the percentage of water present in an oil/water mixture, comprising the steps of:
- a. transmitting the data from the oil/water monitor to a computer means;
- b. comparing the data in the computer means to a predetermined value to determine if the oil or the water is in the continuous phase in the mixture; and
- c. selecting one of two data curves, each of said data curves having an electrical signal plotted against percentage of water, one of said data curves representing water being in the continuous phase in the mixture and the other of said data curves representing oil being in the continuous phase in the mixture; and
- d. reading the selected data curve to determine the percentage of water present in the mixture.

16. In combination with an oil/water monitor which generates data of the electrical properties of an oil/water mixture, a method for determining the percentage of water present in an oil/water mixture, comprising the steps of:
- a. transmitting the data from the oil/water monitor to a computer means;
- b. comparing the data in the computer means to a predetermined value to determine if the oil or the water is in the continuous phase in the mixture;
- c. selecting one of two equations, each of said equations having an electrical property and percentage of water as variables, one of said equations representing water in the continuous phase in the mixture and the other of said equations representing oil in the continuous phase in the mixture;
- d. inserting the data from the oil/water monitor into the selected equation in the computer means; and
- e. solving the equation in the computer means to determine the percentage of water present in the mixture.

* * * * *

REEXAMINATION CERTIFICATE (2101st)
United States Patent [19]
Agar

[11] B1 4,774,680
[45] Certificate Issued Oct. 12, 1993

[54] METHOD AND APPARATUS FOR NET OIL MEASUREMENT

[75] Inventor: Joram Agar, Grand Cayman, Cayman Islands

[73] Assignee: Agar Corporation Ltd., Grand Cayman, Cayman Islands

Reexamination Request:
No. 90/002,684, Mar. 27, 1992

Reexamination Certificate for:
Patent No.: 4,774,680
Issued: Sep. 27, 1988
Appl. No.: 909,626
Filed: Sep. 19, 1986

[51] Int. Cl.$^5$ .............. G01N 15/00; G01N 27/00; G01F 1/74
[52] U.S. Cl. .............. 364/550; 73/61.43; 73/861.04; 324/71.1; 324/698
[58] Field of Search .............. 364/550, 551.01, 496, 364/497, 498, 508; 324/71.1, 76 R, 439, 445, 698; 328/1; 73/61.43, 153, 861.04

[56] References Cited

U.S. PATENT DOCUMENTS

| | | | |
|---|---|---|---|
| 3,006,189 | 10/1961 | Warren et al. | 73/861.04 |
| 3,133,437 | 5/1964 | Remke et al. | 73/53 |
| 3,385,108 | 5/1968 | Rosso | 73/861.04 |
| 4,266,188 | 5/1981 | Thompson | 324/65 R |
| 4,429,273 | 1/1984 | Mazzagatti | 324/61 R |

OTHER PUBLICATIONS

Becher, "Emulsions:Theory and Practice", Second edition, Reinhold Publishing Corp., New York, 1957, pp. 1-3, 84-95, 412-415, 155-169.
Kite, "Instrumentation for Simplified Commingling and Well-Testing Operations", Journal of Petroleum Technology, 1964, pp. 732-738.

Primary Examiner—Thomas G. Black
Attorney, Agent, or Firm—Oblon, Spivak, McClelland, Maier & Neustadt

[57] ABSTRACT

Disclosed is a method and apparatus for measuring the percentages of oil and water present in an oil/water mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixture yields a current output which can be plotted on one of two distinct, empirically or theoretically derived, data curves. One of the data curves represents oil being in the continuous phase and the other data curve represents water being in the continuous phase. A comparator is used to determine whether the oil or the water is in the continuous phase to thereby select the proper data curve on which the energy absorption is plotted. Each of the curves has the energy absorption properties of the media plotted against the percentage of water. Plotting the amount of energy absorbed on the proper curve yields the percentage of water present.

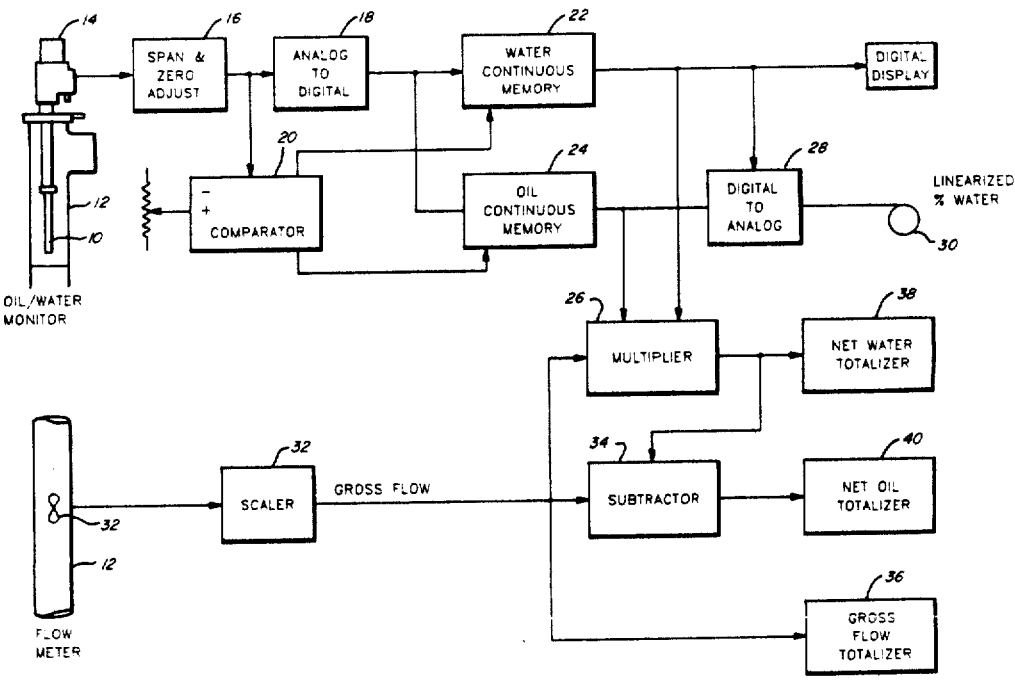

ial property comprises:

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentablility of claims 1–16 is confirmed.

New claims 17–34 are added and determined to be patentable.

17. A method according to claim 2, wherein:
said step of measuring an electrical property comprises measuring at least one electrical property to obtain data on at least two variables related to said oil/water mixture; and said reading step comprises using said data on said at least two variables to determine the percentage of water in the mixture.

18. A method according to claim 17, wherein:
said measuring step comprises measuring first and second electrical properties of said oil/water mixture to obtain said data on said at least two variables;
said step of selecting one of two data curves comprises using the data obtained from the measured first electrical property to select one of two non-linear data curves; and
said reading step comprises using at least the data obtained from the second measured electrical property to read the selected non-linear data curve.

19. A method according to claim 17, wherein said step of selecting one of two data curves comprises using data on one of said at least two variables to select one of two non-linear data curves.

20. A method according to claim 17, wherein the step of measuring an electrical property comprises:
obtaining data on at least two variables derived from at least one electrical property selected from the group consisting of current, voltage, frequency, energy absorption, conductivity, dielectric constant, capacitance, admittance and impedance.

21. A method according to claim 20, wherein said step of measuring an electrical property comprises:
measuring energy absorption of said oil/water mixture to obtain said data on said at least two variables.

22. A method according to claim 7, wherein said step of measuring an electrical property comprises:
obtaining data indicative of the conductivity and the dielectric constant of the oil/water mixture.

23. A method according to claim 21, wherein said step of measuring an electrical property comprises:
obtaining data indicative of the conductivity and the dielectric constant of the oil/water mixture.

24. An apparatus for measuring the percentage of water present in an oil/water mixture flowing in a conduit, comprising:
a probe disposed in the oil/water mixture;
means electrically connected to said probe for measuring at least one electrical property of the mixture to obtain data on at least two variables related to said mixture;
a first memory addressed by the data obtained on said at least two variables for storing data indicative of a non-linear data characteristic representing water being in the continuous phase in the mixture;
a second memory addressed by the data obtained on said at least two variables for storing data indicative of a non-linear data characteristic representing oil being in the continuous phase in the mixture; and
a comparator means for determining whether the oil or the water is in the continuous phase in the mixture by conmparing data obtained on at least one of the variables related to said mixture to a predetermined value, said comparator means selecting said first memory or said second memory based on the comparison so that the selected memory outputs a signal indicative of the flow of water derived from said data curve stored in the selected memory as a function of said data obtained on said at least two variables.

25. An apparatus for measuring the percentage of water in an oil/water mixture flowing through a conduit as recited in claim 24, further comprising:
a flow meter for measuring the gross flow through the conduit; and
a multiplier means receiving data from said first and second memories and said flow meter and thereby obtaining the product of the gross flow and the percentage of water.

26. An apparatus for measuring the percentage of water in an oil/water mixture flowing through a conduit as recited to claim 25, further comprising:
a subtraction means for subtracting the product obtained by said multiplier means from the gross flow.

27. An apparatus for measuring the percentage of water present in an oil/water mixture flowing through a conduit as recited in claim 26, further comprising:
a gross flow totalizer.

28. An apparatus for measuring the percentage of water present in an oil/water mixture as recited in claim 24, further comprising:
an analog-to-digital converter for digitizing the data generated by said means for measuring before it is transmitted to said first and second memories.

29. An apparatus for measuring the percentage of water present in an oil/water mixture as recited in claim 27, further comprising:
a digital-to-analog converter for translating the digitized data from said first and second memories to continuous analog signals.

30. An apparatus for measuring the percentage of water present in an oil/water mixture flowing in a conduit according to claim 24, wherein said measuring means includes means for deriving the two variables related to said mixture by measuring at least one electrical property selected from the group consisting of current, voltage, frequency, energy absorption, conductivity, dielectric constant, capacitance, admittance, and impedance.

31. An apparatus according to claim 24, wherein said measuring means comprises:
means for measuring energy absorption of said oil/water mixture to obtain said data on said at least two variables.

32. An apparatus according to cliam 24, wherein said measuring means comprises:
means for obtaining data indicative of the conductivity and the dielectric constant of the oil/water mixture.

33. An apparatus according to claim 31, wherein said measuring means comprises:

means for obtaining data indicative of the conductivity and the dielectric constant of the oil/water mixture.

34. A comparator circuit for use in determining phase conditions of fluids where there is a pronounced step jump joining two independent curves which represent the electrical properties of an oil/water mixture, said comparator circuit receiving data from an oil/water monitor, comprising:

a. a first memory for storing a first data curve representing a first set of phase characteristics;

b. a second memory for storing a second data curve representing a second set of phase characteristics; and c. a computer means for receiving the data from the oil/water monitor, said computer means comparing the data received to a predetermined value, thereby allowing said computer means to select said first memory if the data received from the oil/water monitor is less than the predetermined value or to select said second memory if the data received from the oil/water monitor is greater than the predetermined value.

* * * * *

(12) EX PARTE REEXAMINATION CERTIFICATE (4967th)
United States Patent
Agar

(10) Number: US 4,774,680 C2
(45) Certificate Issued: Jul. 20, 2004

(54) METHOD AND APPARATUS FOR NET OIL MEASUREMENT

(75) Inventor: Joram Agar, Grand Cayman (KY)

(73) Assignee: Agar Corporation Inc., Houston, TX (US)

Reexamination Request:
No. 90/004,524, Jan. 22, 1997
No. 90/006,236, Mar. 6, 2002

Reexamination Certificate for:
Patent No.: 4,774,680
Issued: Sep. 27, 1988
Appl. No.: 06/909,626
Filed: Sep. 19, 1986

Reexamination Certificate B1 4,774,680 issued Oct. 12, 1993

(51) Int. Cl.[7] .......................... G01N 15/00; G01N 27/00; G01N 27/10; G01F 1/74
(52) U.S. Cl. ..................... 702/25; 73/61.43; 73/61.44; 73/861.04; 324/71.1; 324/698
(58) Field of Search .......................... 73/861.04, 61.43; 702/25; 324/698, 71.1

(56) References Cited

U.S. PATENT DOCUMENTS

| | | |
|---|---|---|
| 3,006,189 A | 10/1961 | Warren et al. |
| 4,048,854 A * | 9/1977 | Herzl ...................... 73/861.04 |
| 4,773,257 A * | 9/1988 | Aslesen et al. ...... 73/861.04 X |
| 4,876,879 A * | 10/1989 | Ruesch ................... 73/861.04 |

OTHER PUBLICATIONS

Engineering Research Assocs., High–Speed Computing Devices 3 (1950).*

Perl, "Complex Microwave Dielectric Properties of Liquids, Solutions and Emulsions", Ph.D. thesis, Illinois Institute of Technology (May 1984).

Chen, "Measurement of Water Content in Oil With Microwave Reflection", East China Petrol. Inst. (vol. 7, No. 3, pp. 376–388, 1983).

Dykesteen et al., "Non–Intrusive Three–Component Ratio Measurement Using an Impedance Sensor", J. Phys. E: Sci Instrum. (vol. 18, pp. 540–544, 1985).

Hanai, "Electrical Properties of Emulsions", (Chapter 5, pp. 353–476), Emulsion Science, edited by P. Sheman (Academic Press, 1962).

E.A. Hammer, "Three–Component Flow Measurement in Oil/Gas/Water Mixtures Using Capacitance Transducers", Ph.D. thesis, University of Manchester, Manchester, UK (Dec. 1983).

"HYFLO Net Oil Computer Series 4300/4301", Bulletin 5120–A, Hydril Control Systems Division, Houston, Texas (1982),

* cited by examiner

*Primary Examiner*—Thomas Noland

(57) ABSTRACT

Disclosed is a method and apparatus for measuring the percentages of oil and water present in an oil/water mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixture yields a current output which can be plotted on one of two distinct, empirically or theoretically derived, data curves. One of the data curves represents oil being in the continuous phase and the other data curve represents water being in the continuous phase. A comparator is used to determine whether the oil or the water is in the continuous phase to thereby select the proper data curve on which the energy absorption is plotted. Each of the curves has the energy absorption properties of the media plotted against the percentage of water. Plotting the amount of energy absorbed on the proper curve yields the percentage of water present.

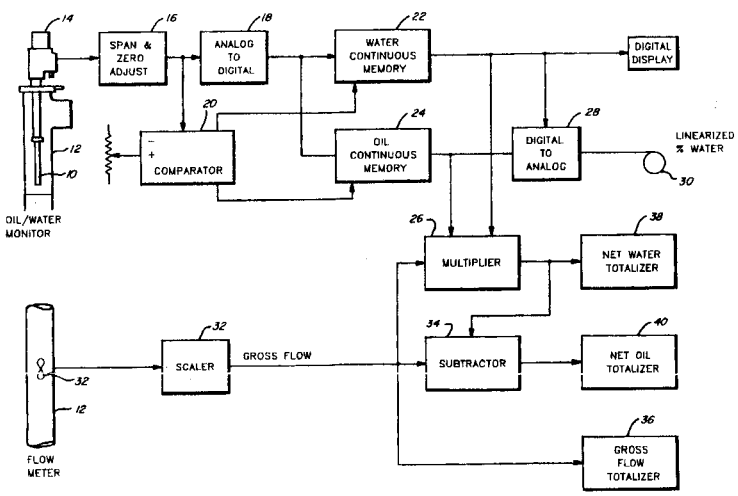

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3, 6–8, 14–16, 23–24, 32 and 34 are determined to be patentable as amended.

Claims 4–5, 9–13, 17–22, 25–31 and 33, dependent on an amended claim, are determined to be patentable.

1. A comparator circuit for use in determining phase conditions of fluids where there is a pronounced step jump joining two *overlapping* independent curves, such as in the electrical properties of an oil/water mixture or the flow characteristics of a fluid, said comparator circuit receiving data from a probe device such as an oil/water monitor or a turbine flow meter, comprising:
    a. a first memory for storing a first data curve representing a first set of phase characteristics;
    b. a second memory for storing a second data curve representing a second set of phase characteristics; and
    c. a computer means for receiving the data from the probe device, said computer means comparing the data received to a predetermined value, thereby allowing said computer means to select said first memory if the data received from the probe device is less than the predetermined value or to select said second memory if the data received from the probe device is greater than the predetermined value.

2. A method for measuring the percentage of water present in a oil/water mixture, comprising the steps of:
    a. measuring an electrical property of the oil/water mixture with an oil/water monitor;
    b. determining whether the oil of the water is in the continuous phase in the mixture;
    c. selecting one of two *overlapping* data curves, each of said data curves having an electrical signal plotted against the percentage of water, one of said data curves representing water being in the continuous phase and the other of said data curves representing oil being in the continuous phase; and
    d. reading the selected data curve to determine the percentage of water pesent in the mixture.

3. A method for measuring the percentage of water present in an oil/water mixture flowing through a conduit, comprising the steps of;
    a. measuring an electrical property of the oil/water mixture with an oil/water monitor;
    b. determining whether the oil or the water is in the continuous phase in the mixture;
    c. selecting one of two *overlapping* data curves, each of said data curves having an electrical signal plotted against the percentage of water, one of said data curves representing water being in the continuous phase and the other of said data curves representing oil being in the continuous phase; and
    d. reading the selected data curve to determine the percentage of water present in the mixture.

6. A method for measuring the percentage of water present in an oil/water mixture utilizing two distinct *overlapping* data curves which represent water being in the continuous phase and oil being in the continuous phase, respectively, comprising the steps of:
    a. measuring an electrical property of the oil/water mixture and generating an electrical signal;
    b. comparing the measured value of the electrical property to a predetermined value for determining whether the oil or the water is in the continuous phase in the mixture, thereby selecting one of the two distinct data curves, each of the two distinct data curves having the electrical signal plotted against percentage of water;
    c. digitizing the electrical signal of the measurement of the electrical property as determined in said measuring step; and
    d. plotting the digitized electrical signal on the curve selected to thereby determine the percentage of water present in the mixture.

7. An apparatus for measuring the percentage of water present in an oil/water mixture, comprising:
    a. a probe disposed in the oil/water mixture;
    b. means for measuring the electrical properties of the oil/water mixture, said means for measuring being electrically connected to said probe;
    c. a first memory for storing a data curve representing water being in the continuous phase in the mixture;
    d. a second memory for storing [a] *an overlapping* data curve representing oil being in the continuous phase in the mixture; and
    e. a comparator means for determining whether the oil or the water is in the continuous phase in the mixture by comparing the amount of energy absorbed to a predetermined value, thereby allowing said comparator means to select said first or said second memory and its respective data curve, each of said data curves having energy absorption plotted against the percentage of water in the mixture.

8. An apparatus for measuring the percentage of water present in an oil/water mixture flowing in a conduit, comprising:
    a. a probe disposed in the oil/water mixture;
    b. means for measuring the electrical properties of the oil/water mixture, said means for measuring being electrically connected to said probe, *where the electrical properties include conductivity and admittance*;
    c. a first memory for storing a data curve representing water being in the continuous phase in the mixture;
    d. a second memory for storing a data curve representing oil being in the continuous phase in the mixture; and
    e. a comparator means for determining whether the oil or the water is in the continuous phase in the mixture by comparing the amount of measured electrical signal to a predetermined value, thereby allowing said comparator means to select said first or said second memory and its respective data curve.

14. A method for linearizing data generated by an oil/water monitor and computing the percentage of water present in an oil/water mixture, comprising the steps of:
    a. transmitting a current into the mixture;

b. measuring an electrical property of the mixture with an oil/water monitor, *where the electrical properties include conductivity and admittance*;

c. comparing the measured electrical property to a predetermined value to thereby select one of two data curves, each curve having an electrical signal plotted against percentages of water, one data curve representing oil in the continuous phase in the mixture and the other data curve representing water in the continuous phase in the mixture; and d. plotting the measured electrical property on the selected curve.

15. In combination with an oil/water monitor which generates data of the electrical properties of an oil/water mixture, a method for determining the percentage of water present in an oil/water mixture, comprising the steps of:

a. transmitting the data from the oil/water monitor to a computer means;

b. comparing the data in the computer means to a predetermined value to determine if the oil or the water is in the continuous phase in the mixture; and c. selecting one of two *overlapping* data curves, each of said data curves having an electrical signal plotted against percentage of water, one of said data curves representing water being in the continuous phase in the mixture and the other of said data curves representing oil being in the continuous phase in the mixture; and d. reading the selected data curve to determine the percentage of water present in the mixture.

16. In combination with an oil/water monitor which generates data of the electrical properties of an oil/water mixture, a method for determining the percentage of water present in an oil/water mixture, comprising the steps of:

a. transmitting the data from the oil/water monitor to a computer means;

b. comparing the data in the computer means to a predetermined value to determine if the oil or the water is in the continuous phase in the mixture;

c. selecting one of two *overlapping* equations, each of said equations having an electrical property and percentage of water as variables, one of said equations representing water in the continuous phase in the mixture and the other of said equations representing oil in the continuous phase in the mixture;

d. inserting the data from the oil/water monitor into the selected equation in the computer means; and e. solving the equation in the computer means to determine the percentage of water present in the mixture.

23. A method [according to claim 21] *for measuring the percentage of water present in a oil/water mixture, comprising the steps of:* a. *measuring an electrical property of the oil/water mixture with an oil/water monitor;* b. *determining whether the oil of the water is in the continuous phase in the mixture;* c. *selecting one of two data curves, each of said data curves having an electrical signal plotted against the percentage of water, one of said data curves representing water being in the continuous phase and the other of said data curves representing oil being in the continuous phase; and* d. *reading the selected data curve to determine the percentage of water pesent in the mixture, said step of measuring an electrical property comprises measuring at least one electrical property to obtain data on at least two variables related to said oil/water mixture; and said reading step comprises using said data on said at least two variables to determine the percentage of water in the mixture, wherein the step of measuring an electrical property comprises: obtaining data on at least two variables derived from at least one electrical property selected from the group consisting of current, voltage, frequency, energy absorption, conductivity, dielectric constant, capacitance, admittance and impedance, wherein said step of measuring an electrical property comprises: measuring energy absorption of said oil/water mixture to obtain said data on said at least two variables,* wherein said step of measuring an electrical property comprises:

obtaining data indicative of the conductivity and the dielectric constant of the oil/water mixture.

24. An apparatus for measuring the percentage of water present in an oil/water mixture flowing in a conduit, comprising:

a probe disposed in the oil/water mixture;

means electrically connected to said probe for measuring at least one electrical property of the mixture to obtain data on at least two variables related to said mixture;

a first memory addressed by the data obtained on said at least two variables for storing data indicative of a non-linear data characteristic representing water being in the continuous phase in the mixture;

a second memory addressed by the data obtained on said at least two variables for storing *overlapping* data indicative of a non-linear data characteristic representing oil being in the continuous phase in the mixture; and a comparator means for determining whether the oil or the water is in the continuous phase in the mixture by [conmparing] *comparing* data obtained on at least one of the variables related to said mixture to a predetermined value, said comparator means selecting said first memory or said second memory based on the comparison so that the selected memory outputs a signal indicative of the flow of water derived from said data curve stored in the selected memory as a function of said data obtained on said at least two variables.

32. An apparatus [according to cliam 24] *for measuring the percentage of water present in an oil/water mixture flowing in a conduit, comprising:* a *probe disposed in the oil/water mixture;*

*means electrically connected to said probe for measuring at least one electrical property of the mixture to obtain data on at least two variables related to said mixture;* a *first memory addressed by the data obtained on said at least two variables for storing data indicative of a non-linear data characteristic representing water being in the continuous phase in the mixture;* a *second memory addressed by the data obtained on said at least two variables for storing data indicative of a non-linear data characteristic representing oil being in the continuous phase in the mixture; and* a *comparator means for determining whether the oil or the water is in the continuous phase in the mixture by comparing data obtained on at least one of the variables related to said mixture to a predetermined value,*

*said comparator means selecting said first memory or said second memory based on the comparison so that the selected memory outputs a signal indicative of the flow of water derived from said data curve stored in the selected memory as a function of said data obtained on said at least two variables,* wherein said measuring means comprises:

means for obtaining data indicative of the conductivity and the dielectric constant of the oil/water mixture.

34. A comparator circuit for use in determining phase conditions of fluids where there is a pronounced step jump joining two independent *overlapping* curves which represent the electrical properties of an oil/water mixture, said comparator circuit receiving data from an oil/water monitor, comprising:

a. a first memory for storing a first data curve representing a first set of phase characteristics;

b. a second memory for storing a second data curve representing a second set of phase characteristics; and c. a computer means for receiving the data from the oil/water monitor, said computer means comparing the data received to a predetermined value, thereby allowing said computer means to select said first memory if the data received from the oil/water monitor is less than the predetermined value or to select said second memory if the data received from the oil/water monitor is greater than the predetermined value.

\* \* \* \* \*